United States Patent [19]

Lam

[11] 4,038,031

[45] July 26, 1977

[54] TEST COMPOSITION, DEVICE AND METHOD FOR DETECTING BILIRUBIN

[75] Inventor: Charles T. W. Lam, Elkhart, Ind.

[73] Assignee: Miles Laboratories, Inc., Elkhart, Ind.

[21] Appl. No.: 618,802

[22] Filed: Oct. 2, 1975

[51] Int. Cl.² .................... G01N 21/06; G01N 33/16
[52] U.S. Cl. ............... 23/230 B; 23/253 TP; 252/408
[58] Field of Search .............. 23/230 B, 253 TP; 252/408

[56] References Cited

U.S. PATENT DOCUMENTS

| 2,854,317 | 9/1958 | Free et al. ...................... 23/230 B |
| 3,526,479 | 9/1970 | Rey et al. ...................... 23/230 B |
| 3,585,001 | 6/1971 | Mast ............................... 23/230 B |

OTHER PUBLICATIONS

Chem. Abstr., v. 19:14525, (1925).
Quigley, Anal. Chem., v. 24, pp. 1859-1860, (1952).
Merck Index, 8th Ed., pp. 188, 401 relied upon, (1968).

Primary Examiner—Morris O. Wolk
Assistant Examiner—Sidney Marantz
Attorney, Agent, or Firm—Andrew L. Klawitter

[57] ABSTRACT

A test composition, device, and method for detecting bilirubin in urine. The test composition includes a diazonium compound reactable with urinary bilirubin to produce a color change, an acid pH producing constituent, and a potentiating agent for the test reaction. The potentiating agent is an adduct of a ureido compound and an organic sulfonic acid or a salt form thereof. Particularly useful as the ureido constituent of the adduct are urea and substituted and unsubstituted cyclic ureido compounds, particularly those belonging to the xanthine family. The test device comprises a carrier, such as an absorbent matrix, incorporated with the test composition. The test method is carried out by contacting a urine test sample with the test composition and observing any resulting colorimetric response.

33 Claims, No Drawings

TEST COMPOSITION, DEVICE AND METHOD FOR DETECTING BILIRUBIN

BACKGROUND OF THE INVENTION

1. Field of the Invention

The present invention concerns an improved test composition, device, and method for the detection of bilirubin in urine.

The diagnostic value of the determination of bilirubin in urine is well known. Urine from a normal subject does not contain an appreciable amount (less than 0.05 mg/100 ml) of bilirubin. However, various diseased conditions, such as biliary obstruction and hemolytic and hepatic diseases, cause bilirubin to appear in urine at an abnormally high concentration. It is generally recognized that the presence of bilirubin in urine at a concentration above 0.05 mg/100 ml indicates an abnormal clinical status requiring the performance of more comprehensive diagnostic procedures in order to determine the specific causative disease.

It is generally recognized that essentially all bilirubin that appears in pathological urine is in a conjugated form. Bilirubin is a degradation product of the heme moiety of hemoglobin and, once formed in the blood stream, is taken up by the liver where it becomes conjugated through esterification with glucuronic acid. The resulting bilirubin glucuronides are extremely water soluble, in contrast to free bilirubin which is highly insoluble in water. The conjugated bilirubins are thus able freely to pass from the liver to the kidneys where under normal clinical conditions, essentially all conjugated bilirubin is converted to urobilinogen and excreted as a consitutuent of urine. In the various pathological conditions, conjugated bilirubin is itself excreted in the urine.

2. Brief description of the prior art

Bilirubin is conventionally determined in routine urinalysis based on its reaction with various diazonium compounds in an acidic medium to form a colored azobilirubin complex. While several test formats are reported in the literature, the most commonly used test format in the clinical laboratory is that generally referred to as a test strip. The diazonium compound is incorporated in a carrier capable of absorbing a predetermined amount of urine when dipped momentarily into a urine sample. Any resulting colorimetric response may be read in less than one minute. The preparation and use of a bilirubin test strip is described in detail in U.S. Pat. No. 3,585,001. While the test strips which have been described in the art provide very rapid and convenient means for detecting urinary bilirubin, it is generally known that the available test strips are not sufficiently sensitive to detect levels of bilirubin only slightly elevated from the normal level, i.e. between 0.05 and 0.8 mg bilirubin per 100 ml.

There have been a few reported attempts to increase the sensitivity of the reaction between diazonium compounds and urinary bilirubin; however, the test systems that have resulted have certain disadvantages.

U.S. Pat. No. 3,880,588 describes a class of diazonium compounds designed to enhance the colorimetric response of the azobilirubin complex and to decrease interfering color reactions with urobilinogen, which is structurally and chemically very similar to bilirubin. The described diazonium compounds, unlike the conventional compounds, form interfering colored products with such constituents of urine as homogentisic acid and 5-hydroxyindole-3-acetic acid. The latter is a normal constituent of urine and as little as 1 mg/100 ml of such constituent in urine causes false positive results using the diazonium compounds described in this patent.

Another attempt to increase the sensitivity of the test strip-incorporated diazonium reagents is described in U.S. Pat. No. 3,853,476 which discloses the use of certain phosphoric acid diesters as sensitizing or potentiating agents for the reaction between the diazonium compound and bilirubin. However, due to the incompatibility between the phosphoric acid diesters and aqueous media, test strips prepared according to this patent must be manufactured by a double-impregnation process.

It should be mentioned that various so-called "accelerating agents" have been described in the art relative to the detection of bilirubin in serum by the diazo-coupling reaction. Such agents have included caffeine, dyphylline, sodium acetate, sodium benzoate, gum arabic, and various other chemically unrelated compounds. The use of such accelerating agents in serum bilirubin tests was described in the literature as early as the 1920's but has never been applied in general to urinary bilirubin tests. This has been due to the generally recognized fact that such accelerating agents act on a form of bilirubin that is not present in significant amounts in urine. Such accelerators are reported to promote the diazocoupling of free bilirubin. No effect on the coupling of conjugated bilirubin has been reported, since in serum bilirubin tests the conjugated forms of bilirubin react relatively rapidly with the diazonium compounds without the need for accelerators. Hence, the conjugated forms of bilirubin in serum are referred to as direct-reacting bilirubin, whereas free bilirubin, which requires the presence of an accelerator in order to react rapidly, is referred to as indirect-reacting bilirubin. The fact that the scientific community views the effect of the reported accelerating agents as being restricted to the diazo-coupling reaction of free bilirubin, and not applicable to the reaction with conjugated bilirubin, is well supported by the concurrence of the primary review publications considered authorative in the art. For example, reference may be made to Henry, R. J., Clinical Chemistry, Principles and Technics, Harper and Row (1964) pp. 577-583; With. T. K., Bile Pigments, Academic Press (1968) pp. 324-327; and the Journal of American Medical Technologists, volume 31 (1969) pp. 707-710.

A single investigator has reported the use of dyphylline in a urinary bilirubin determination — Scandanavian Journal of Clinical Laboratory Investigation, supplement 56 (1961). However, such use was specifically designed to accomplish the same effect as discussed in the literature relative to serum bilirubin tests, namely, to accelerate the diazo-coupling of free bilirubin which, as is known, could only be present in the urine tested in very small amounts. The described procedure involves a cumbersome liquid test system, and there is no suggestion of a rapid and sensitive test strip system. Moreover, the described procedure has received little attention from those skilled in the art in their development of more sensitive bilirubin test strips, as is evidenced by their resort to the disadvantageous test systems disclosed in the previously discussed U.S. Pat. Nos. 3,853,476 and 3,880,588.

SUMMARY OF THE INVENTION

It has now been found that adducts of ureido compounds with organic sulfonic acids or salts have a potentiating effect on the test reaction between a diazonium compound and urinary bilirubin in an acidic environment. The ureido adduct constituent may be urea, an acyclic lower alkyl derivative of urea, or a cyclic ureido compound or a derivative thereof. A cyclic ureido compound or a derivative thereof is preferred, and one which belongs to the xanthine family is especially preferred.

The test composition of the present invention thus comprises a diazonium compound which reacts with urinary bilirubin to produce a color change, a constituent capable of producing an acidic pH in the urine sample, and the potentiating agent. The test composition may be in a dry or liquid form and preferably is incorporated with a carrier, such as an absorbent matrix, in the form of a test strip device. The test method may be carried out by contacting a urine test sample with the elements of the test composition, singularly or in combination, such as by contact with the carrier of the preferred test strip device, and observing any resulting colorimetric response.

DESCRIPTION OF THE PREFERRED EMBODIMENTS

The presence of the adduct of the present invention, hereinafter referred to at times as the potentiating agent, causes the formation of more intensely colored azobilirubin complexes, thereby effectively increasing the sensitivity of the test reaction. Additionally, the potentiating agent has been found to have a bathochromic effect on the test reaction in that the azobilirubin complexes formed in its presence generally have altered absorbance spectra resulting in colors that are more easily distinguishable from expected interfering color formations. Even further, the potentiating agent has also been found to act as a stabilizer for the diazonium compound, particularly when the test composition is incorporated with a carrier in a dry state.

These performance advantages are complemented by manufacturing advantages as well. In preparing the preferred test strip device, the carrier is usually incorporated with the test composition either by saturating the carrier with a solution of the test composition, followed by drying, or by forming the carrier in the presence of a solution of the test composition, followed by a curing process. In the past, in order to prepare the test strip device according to the first mentioned method, several saturating and drying steps were necessary. As explained in detail in U.S. Pat. No. 3,585,004, in order to incorporate a sufficient amount of the acid constituent with the carrier according to the known methods a specially designed acid releasing compound had to be used. Since such compound was designed to release a mineral acid upon aqueous contact, it could not be included in the initial diazonium salt solution impregnated into the carrier. The multiple saturation manufacturing technique is not necessary if the potentiating agent of the present invention is included in the initial diazonium salt solution, since less acid is needed to obtain sensitive test results, and the necessary amount of acid can be provided by the use of a solid acid, such as an organic acid.

The present invention thus provides an improved test composition, device, and method for detecting bilirubin in a urine test sample and is characterized by increased sensitivity of the diazo-coupling reaction, increased stability of the dry forms of the test composition, decreased interference from extraneous constituents of urine, and simplification of the method of manufacture of the preferred test strip device.

Various ureido compounds have been found to be useful in forming the potentiating agent of the present invention. In the context of this disclosure, ureido compounds include those compounds which contain the group

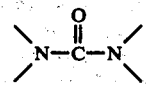

hereinafter referred to as a ureido group. Ureido compounds as a class therefore include urea and its various derivatives. Cyclic ureido compounds, characterized by a heterocyclic ring which includes a ureido group, are especially useful. Exemplary of such cyclic ureido compounds are cytosine, which is an amino-substituted 2-oxopyrimidine, and 2-imidazolidone, as well as other 5 and 6 member oxoheterocyclic ureido compounds. Particularly useful cyclic ureido compounds are those having a dioxoheterocyclic ring structure of the formula

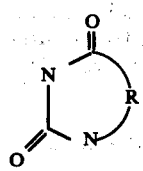

(I)

or a tautomeric form thereof, wherein R is a linking group forming a 5 or 6 member ring and wherein the heterocyclic ring may contain substituents that do not substantially impair the desired potentiating effect. Substituents other than hydrogen may be attached to the nitrogen atoms in the heterocyclic ring structure and are usually substituted or unsubstituted lower alkyl groups, i.e. containing 1–5 carbon atoms. A wide variety of substituents may be attached to the linking group R, since it is theorized that the potentiating effect is due primarily to the presence of the ureido group. Such substituents usually hydrogen, alkyl, halogeno, and substituted or unsubstituted fused-ring isocyclic or heterocyclic aliphatic or aromatic systems. Examples of useful compounds having formula (I) are the substituted and unsubstituted 3,5-dioxo-1,2,4-triazoles such as urazole, the substituted and unsubstituted 2,4,5-trioxoimidazoles such as parabanic acid, and the substituted and unsubstituted 2,5-dioxoimidazoles such as 1-methyl hydantoin and 7,8-benzo-1,3-diazaspiro [4,5] decane-2,3-dione.

Compounds of formula (I) that are preferred are 2,6-diozopyrimidines and derivatives thereof such as uridine. Of the 2,6-dioxopyrimidines, particularly preferred are those compounds having the formula (II)

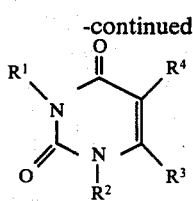

or a tautomeric form thereof, wherein $R^1$ and $R^2$ are respectively hydrogen or a lower alkyl group, and wherein $R^3$ and $R^4$ (1) are respectively hydrogen, halogeno, or a lower alkyl group or (2) together with the ethylene link in the heterocyclic ring system form a substituted or unsubstituted isocyclic or heterocyclic ring system which does not substantially impair the desired potentiating effect. Compounds of formula (II) include 5-bromouracil, 1,3-dimethyl-6,7-diphenylumazine, and xanthine and derivatives thereof.

Of the cyclic ureido compounds, the most preferred are xanthine and its derivatives which have the formula

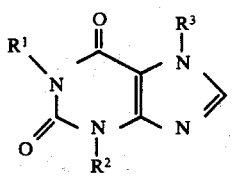

(III)

or a tautomeric form thereof, wherein $R^1$ and $R^2$ are respectively hydrogen or a lower alkyl group and wherein $R^3$ is hydrogen, a lower alkyl group, or a hydroxy-substituted lower alkyl group. These compounds are preferred because of their particular added stabilizing effect on the diazonium compound and include caffeine, dyphylline, and 3-isobutyl-1-methyl xanthine.

Other ureido compounds may be used as well, so long as the desired potentiating effect is produced by the adducts they form with an organic sulfonic acid or salt. In addition to urea itself, the acyclic lower alkyl derivatives of urea have been found to be useful as a constituent of the potentiating agent. An example of a useful acyclic lower alkyl derivative of urea is tetramethylurea. The skilled artisan will recognize that various ureido compounds other than those specifically described in this disclosure are useful as a constituent of the potentiating agents within the scope of the present invention.

Having discussed the ureido adduct constituent of the potentiating agent, the complementary adduct constituent may include any organic compound containing one of more sulfonic acid groups, or a salt form or forms thereof, which is capable of combining with the selected ureido compound to form a water soluble adduct having the desired potentiating effect. Such compounds have the general formula

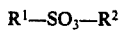

wherein $R^1$ is an organic skeleton and $R^2$ is hydrogen, to form a sulfonic acid group, or a salt-forming constituent, usually an inorganic cation such as an alkali metal, i.e. sodium, potassium, and so forth. The aromatic sulfonic acids and salt forms thereof are preferred since they additionally aid in stabilizing the diazonium component both in its dry form when in combination with the potentiating agent and in its solution form such as it exists during the manufacturing process. Aromatic sulfonic acids and their salt forms are known stabilizers of diazonium salt solutions. Particularly useful aromatic sulfonic acids and salt forms thereof are sulfosalicylic acid; the naphthalenedisulfonic acids, such as 1,5-naphthalenedisulfonic acid; and the biphenyldisulfonic acids, such as 4,4'-biphenyldisulfonic acid; and salt forms thereof.

The diazonium compound included in the test composition may be any of the well known diazonium compounds, usually in the form of salts, which couple with urinary bilirubin to form a colored complex, thereby producing a color change. Generally, the most advantageous diazonium compounds are the aryldiazonium compounds which include the diazotized forms of 2,4-dichloroaniline; para-nitroaniline; para-chloroaniline; 2,5-dichloroaniline; 4-chloro-o-anisidine; 3,3'-dimethoxy benzidine; and 2-methoxy-5-nitroaniline. Other diazonium compounds disclosed in the art as being capable of coupling with urinary bilirubin may be utilized as well.

A stabilizer for the diazonium compound may also be included in the test composition. Such a stabilizer serves to inhibit interfering diazo-coupling reactions by occupying the anionic portion of the diazonium compound as described more fully in U.S. Pat. No. 3,814,586. Additionally such stabilizer aids in maintaining the diazonium compound in a dissolved state during the preparation of the test composition and the test device and during the test reaction. The stabilizer may be selected from a wide range of compounds such as fluoroborates; transition metal halogeno compounds, such as zinc and cobalt chlorides; and aromatic and aliphatic sulfonic acids and salts, including those previously mentioned as preferred constituents of the potentiating agent.

The acid pH producing constituent of the test composition may consist of a compound or mixture of compounds capable of producing an acidic pH in the urine sample being tested. An acidic environment for the test reaction is known to decrease ascorbic acid interference, to stabilize the colored azobilirubin complex, and to elevate the molar extinction coefficient of the complex for enhancement of the colorimetric response. A preferred strongly acidic environment is obtained when the acid pH producing constituent yields a pH of less than 3 at a concentration of 0.1 N. Where the acid pH producing constituent consists of a solid acid, such as an organic acid as is preferred, such acid preferably has a $pK_a$ of less than about 4. Exemplary of useful organic acids are citric acid, sulfosalicyclic acid, tartaric acid, succinic acid, cyclohexanesulfamic acid, and maleic acid. Where the acid constituent contains a sulfonic acid group, as in the case of sulfosalicylic acid, such compound may also serve as a constituent of the potentiating agent and/or as a stabilizer for the diazonium compound. Thus, where the test composition is prepared from a solution of the diazonium compound, the acid pH producing constituent, and the potentiating agent, a sufficient excess of an organic sulfonic acid or salt thereof would provide a source of material to function as the acid pH producing constituent, a diazonium stabilizer, and the organic acid or salt adduct constituent of the potentiating agent.

Optional materials may also be included in the test composition. Surfactants may be included in order to increase the wettability of the test composition with respect to the urine test sample. The test composition may be in the form of an aqueous solution or a dry form such as a powder or tablet. If in tablet form, the test composition preferably includes an effervescent couple to aid disintegration of the tablet upon contact with the test sample. Inert fillers to assist the formation of the table may also be included in the test composition. Solubilizing agents may be included in test compositions in liquid form or incorporated with a carrier. Such solubilizing agents prevent the precipitation of the active test composition ingredients during preparation of the test device and during the test reaction. An example of a solubilizing agent is the compound sold under the trademark Gantrez by the General Aniline and Film Corporation of New York. This compound is an equimolar copolymer of methylvinyl ether and maleic anhydride and in solution form has a solubilizing effect, particularly with respect to the potentiating agent. The proportion of ingredients in the test composition may vary widely depending on the form thereof used and the test procedure to be followed. The following is a table of the generally allowable and preferable proportions of ingredients for the test composition in dry form, such as it exists in the test device, expressed as percent by weight:

|  | allowable range | preferred range |
|---|---|---|
| diazonium compound | 0.05–10 | 0.2–2 |
| acidic constitutent | 1–80 | 20–50 |
| potentiating agent | 5–80 | 30–60 |
| stabilizing agent | 0–50 | 1–15 |
| solubilizing agent | 0–30 | 2–10 |

The preferred form of the test composition is that of the test device. Incorporation of the test composition with a carrier provides a convenient device, particularly when in the form of a test strip, for contacting the test sample with the test composition and for reading the result. The carrier is usually in the form of a matrix capable of receiving and retaining a predetermined volume of the urine test sample. Such a matrix may be composed of a bibulous paper, a porous polymeric membrane, a water swellable gel, an absorbent, inert woven or non-woven fabric, and so forth. The test composition may be incorporated with the carrier by means of imregnantion or by means of chemical or physical bonding, or as a result of formation of the carrier in the presence of a solution of the test composition. The carrier is usually attached to or otherwise associated with a holder or support, such as an inert plastic strip, to form the test device and provide convenient means for manipulating the carrier in the analysis of a urine test sample.

The test method, in its most fundamental sense, involves contacting the test sample with the test composition, preferably by use of the test device, and observing any resulting colorimetric response either visually or by means of an instrument. The test sample usually takes the form of raw urine; however, in special circumstances diluted or treated urine may comprise the urine test sample.

The present invention is described herein provides a test composition, device, and method capable of detecting urinary bilirubin to a sensitivity of 0.1 mg per 100 ml in less than one minute. The test composition retains its sensitivity for up to 3 months of 40° C dry form. It has been found by analytical techniques that the decomposition of the diazonium compound in the dry test composition of the present invention is much less than that in test compositions which do not contain the potentiating agent. The use of the potentiating agent allows the use of the conventional diazonium compounds which are least subject to interference from extraneous constituents of urine without sacrificing sensitivity. In addition, the use of the potentiating agent allows manufacture of the test device of the present invention in a manner more convenient than that required for prior art devices containing phosphoric acid diesters as sensitizing agents.

The present invention will now be illustrated, but is not intended to be limited, by the following Examples.

EXAMPLE 1

Spot plate test demonstrating the effect of potentiating agents of the present invention on the reaction between a diazonium compound and urinary bilirubin.

To fourteen wells in a spot plate were added 3 drops of an aqueous solution having the following formulation:

| | |
|---|---|
| 2,4-dichloroaniline | 0.075 gm |
| 1,5-naphthalenedisulfonic acid sodium salt | 0.6 gm |
| sulfosalicylic acid | 7 gm |
| sodium nitrite | 0.1 gm |
| distilled water | 100 ml |

To thirteen of the wells were then separately added urea and the various urea derivatives listed in Table 1, thus forming sulfonic acid adducts thereof. The resulting test solutions had a yellowish color and upon addition of urinary bilirubin produced shades of purple. A drop of a urine specimen containing a pathological amount of urinary bilirubin was added to each of the fourteen wells and the intensity of the color change in each well was recorded in relative arbitrary units assigned by the observer with zero indicating no color change. The results are shown in Table 1.

TABLE 1

| Ureido Adduct Constituent | Intensity of Color Change |
|---|---|
| none | 5 |
| urea | 20 |
| tetramethylurea | 10 |
| urazole | 20 |
| 2-imidazolidone | 25 |
| caffeine | 10 |
| dyphylline | 8 |
| uridine | 8 |
| 1,3-dimethyl-6,7-diphenyllumazine | 8 |
| 5-bromouracil | 8 |
| 7,8-benzo-1,3-diazaspiro[4,5] decane-2,4-dione | 8 |
| parabanic acid | 8 |
| 1-methylhydantoin | 6 |
| uracil | 6 |

EXAMPLE 2

Preparation and use of test devices embodying the present invention and demonstrating the effect of potentiating agents of the present invention on the reaction between a diazonium compound and urinary bilirubin.

A standard diazonium salt solution was prepared by combining the following ingredients:

| | |
|---|---|
| 2,4-dichloroaniline | 1.125 gm |
| 1,5-naphthalene disulfonic acid sodium salt | 9 gm |
| sulfosalicylic acid | 105 gm |

-continued

| | |
|---|---|
| sodium nitrite | 1.5 gm |
| Gantrez* (10% aqueous solution) | 150 ml |
| methanol | 750 ml |
| distilled water | 600 ml |

*an equimolar copolymer of methylvinyl ether and maleic anhydride available from the General Aniline and Film Corporation, New York.

Ten 50 ml portions of the standard diazonium salt solution were placed in separate beakers. To nine of the beakers was then separately added the various ureido compounds listed in Table 2, thus forming sulfonic acid adducts thereof. Separate sections of S&S 470 paper, manufactured by Schleicher and Schuell, Inc., Keene, New Hampshire, were respectively saturated with the ten beaker solutions and dried. The respective reagent-impregnated paper sections, which had a slightly yellowish color, were cut into roughly 5mm square pads which were then attached to plastic strips with double-faced adhesive tape. Three of each of the resulting ten sets of reagent strips were separately immersed momentarily into three urine specimens containing 0.0, 0.4, and 1.6 mg of urinary bilirubin per 100 ml, respectively. The intensity of the color change on the pads was recorded in relative arbitrary units assigned by the observer with zero indicating no color change. The results are given in Table 2.

TABLE 2

| Ureido Adduct Constituent | Amount Added To 50 ml of Standard Solution (gm) | Observed Reacted Color | Intensity of Color Change bilirubin conc. (mg/100 ml) | | |
|---|---|---|---|---|---|
| | | | 0.0 | 0.4 | 1.6 |
| none | — | purple | 0 | 5 | 25 |
| caffeine | 5 | purple | 0 | 10 | 30 |
| 5-bromouracil | 4 | purple | 0 | 10 | 30 |
| 7,8-benzo-1,4-diazaspiro [4,5] decane-2,4-dione | 5 | blue | 0 | 10 | 30 |
| 1,3-dimethyl-6,7-diphenyllumazine | 1 | blue | 0 | 12 | >30 |
| 1-methylhydantoin | 5 | blue | 0 | 8 | 28 |
| parabanic acid | 5 | purple | 0 | 10 | >30 |
| uridine | 5 | purple | 0 | 13 | >30 |
| urea | 5 | blue | 2 | 9 | 30 |
| 3-isobutyl-1-methyl xanthine | 1 | blue | 0 | 11 | >30 |

EXAMPLE 3

Preparation and use of test devices demonstrating the effect of potentiating agents of the present invention on the reaction between a diazonium compound and urinary bilirubin.

A standard diazonium salt solution was prepared by combining the following ingredients:

| | |
|---|---|
| para-nitroaniline | 0.75 gm |
| 1,5-naphthalenedisulfonic acid sodium salt | 6 gm |
| sulfosalicylic acid | 70 gm |
| sodium nitrite | 1.0 gm |
| Gantrez (5% aqueous solution) | 200 ml |
| methanol | 500 ml |
| distilled water | 300 ml |

*an equimolar copolymer of methylvinyl ether and maleic anhydride available from the General Aniline and Film Corporation, New York.

Four 50 ml portions of the standard diazonium salt solution were placed in separate beakers. To three of the beakers 5 gm of the various ureido compounds listed in Table 3 were respectively added, thus forming sulfonic acid adducts thereof. Separate sections of S&S 470 paper, manufactured by Schleicher and Schuell, Inc., Keene, New Hampshire, were saturated respectively with the four beaker solutions and dried. The respective reagent-impregnated paper sections, which had a yellowish color, were cut into roughly 5 mm square pads which were then attached to plastic strips with double-faced adhesive tape. Five of each of the resulting four sets of reagent stips were separately immersed momentarily into five urine specimens containing 0.0, 0.2, 0.4, 0.8, and 1.6 mg of urinary bilirubin per 100 ml respectively. The intensity of the color change on the pads was recorded as in Example 2. The reacted color of the pads were shades of purple. The results are shown in Table 3.

TABLE 3

| Ureido Adduct Constituent | Intensity of Color Change bilirubin conc. (mg/100 ml) | | | | |
|---|---|---|---|---|---|
| | 0.0 | 0.2 | 0.4 | 0.8 | 1.6 |
| none | 0 | 0 | 0 | 5 | 10 |
| caffeine | 0 | 2 | 10 | 15 | 20 |
| parabanic acid | 0 | 2 | 10 | 15 | 20 |
| uridine | 0 | 2 | 10 | 15 | 20 |

EXAMPLE 4

Demonstration of the criticality of using an organic acid or salt which contains a sulfonic acid group, or salt form thereof, in forming the adduct intended to have a potentiating effect on the reaction between a diazonium compound and urinary bilirubin.

A standard diazonium salt solution was prepared by combining the following ingredients:

| | |
|---|---|
| 2,4-dichloroaniline | 0.5 gm |
| oxalic acid | 35 gm |
| sodium nitrite | 0.5 gm |
| methanol | 250 ml |
| distilled water | 250 ml |

Four 50 ml portions of the standard diazonium salt solution were placed in separate beakers. To three of the beakers were respectively added 5 gm of the various ureido compounds listed in Table 4, thus forming oxalic acid adducts thereof. Separate sections of S&S 470 paper, manufactured by Schleicher and Schuell, Inc., Keene, New Hampshire, were respectively saturated with the four beaker solutions and dried. The respective reagent-impregnated paper sections, which had a yellowish color, were cut into roughly 5 mm square pads which were then attached to plastic strips with double-faced adhesive tape. Three of each of the resulting four sets of reagent strips were separately immersed momentarily into three urine specimens containing 0.0, 0.4, and 1.6 mg bilirubin per 100 ml respectively. The intensity of the color change was recorded as in Example 2. The reacted colors of the pads were shades of purple. The results are given in Table 4.

TABLE 4

| Ureido Adduct Constituent | Intensity of Color Change bilirubin conc. (mg/100 ml) | | |
|---|---|---|---|
| | 0.0 | 0.4 | 1.6 |
| none | 0 | 8 | 28 |
| caffeine | 0 | 8 | 28 |
| 7,8-benzo-1,3-diazaspiro [4,5] decane-2,4-dione | 0 | 8 | 28 |
| parabanic acid | 0 | 8 | 28 |

It can thus be seen that the ureido compound — oxalic acid adducts did not have any potentiating effect on the reaction between the diazonium compoound and urinary bilirubin, whereas it was demonstrated in Examples 2 and 3 that the ureido compound — sulfonic acid adducts did act as potentiating agents for the test reaction.

What is claimed is:

1. A test composition for detecting bilirubin in a urine sample, which composition comprises a diazonium compound which reacts with urinary bilirubin to produce a color change; a constituent capable of producing an acidic pH in said urine sample; and an organic sulfonic acid or an organic sulfonic acid salt adduct of urea or of a derivative of urea, which adduct has a potentiating effect on reaction of said diazonium compound with urinary bilirubin in an acidic environment.

2. A test composition as claimed in claim 1 wherein said derivative of urea is an acyclic lower alkyl derivative of urea.

3. A test composition as claimed in claim 1 wherein said derivative of urea is a cyclic ureido compound or a derivative thereof.

4. A test composition as claimed in claim 3 wherein said cyclic ureido compound or derivative thereof has a dioxohetercyclic ring structure of the formula

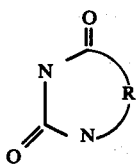

or a tautomeric form thereof, wherein R is a linking group forming a 5 or 6 member ring and wherein the heterocyclic ring may contain substituents that do not substantially impair said potentiating effect.

5. A test composition as claimed in claim 1 wherein said derivative of urea is 2,6-dioxopyrimidine or a derivative thereof.

6. A test composition is claimed in claim 1 wherein said derivative of urea is selected from the group consisting of compounds having the formula

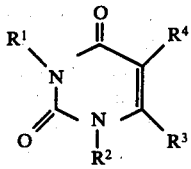

or a tautomeric form thereof, wherein R¹ and R² are respectively hydrogen or a lower alkyl group and wherein R³ and R⁴ (1) are respectively hydrogen, halogeno, or a lower alkyl group or (2) together with the ethylene link in the heterocyclic ring form an isocyclic or heterocyclic ring system which does not substantially impair said potentiating effect.

7. A test composition as claimed in claim 6 wherein the organic sulfonic acid or the organic sulfonic acid salt constituent of said adduct is aromatic.

8. A test composition as claimed in claim 1 wherein said derivative of urea is selected from the group consisting of compounds having the formula

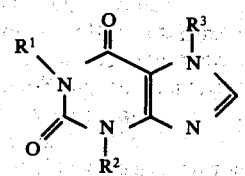

or a tautomeric form thereof, wherein R¹ and R² are respectively hydrogen or a lower alkyl group and wherein R³ is hydrogen, a lower alkyl group, or a hydroxy-substituted lower alkyl group.

9. A test composition as claimed in claim 8 wherein the organic sulfonic acid or the organic sulfonic acid salt constituent of said adduct is aromatic.

10. A test composition as claimed in claim 1 wherein said urea derivative is selected from the group consisting of caffeine, dyphylline, uridine, urazole, 2-imidazolidone, and parabanic acid.

11. A test composition as claimed in claim 10 wherein the organic sulfonic acid or the organic sulfonic acid salt constituent of said adduct is aromatic.

12. A test composition is claimed in claim 1 wherein said urea derivative is caffeine.

13. A test composition as claimed in claim 12 wherein the organic sulfonic acid or the organic sulfonic acid salt constituent of said adduct is aromatic.

14. A test composition as claimed in claim 12 wherein the organic sulfonic acid or the organic sulfonic acid salt constituent of said adduct is sulfosalicylic acid or a salt form thereof.

15. A test composition as claimed in claim 1 wherein said diazonium compound is an aryldiazonium salt.

16. A test composition as claimed in claim 15 wherein said aryldiazonium salt is a 2,4-dichlorobenzenediazonium salt.

17. A test composition as claimed in claim 1 wherein the organic sulfonic acid or the organic sulfonic acid salt constituent of said adduct is aromatic.

18. A test composition as claimed in claim 17 wherein said aromatic sulfonic acid is selected from the group consisting of sulfosalicylic acid, naphthalenedisulfonic acids, and biphenyldisulfonic acids.

19. A test composition as claimed in claim 1 wherein said constituent capable of producing an acidic pH in said urine sample is an organic acid.

20. A test composition as claimed in claim 19 wherein said organic acid has a pK$_a$ of less than about 4.

21. A test device for detecting bilirubin in urine, which device comprises the test composition of claim 1 and a carrier therefor.

22. A test device for detecting bilirubin in urine, which device comprises the test composition of claim 6 and a carrier therefor.

23. A test device for detecting bilirubin in urine, which device comprises the test composition of claim 8 and a carrier therefor.

24. A test device for detecting bilirubin in urine, which device comprises the test composition of claim 9 and a carrier therefor.

25. A test device for detecting bilirubin in urine, which device comprises the test composition of claim 11 and a carrier therefore.

26. A test device for detecting bilirubin in urine, which device comprises the test composition of claim 12 and a carrier therefor.

27. A test device for detecting bilirubin in urine, which device comprises the test composition of claim 13 and a carrier therefor.

28. A test device for detecting bilirubin in urine, which device comprises the test composition of claim 17 and a carrier therefor.

29. A test device for detecting bilirubin in urine, which device comprises the test composition of claim 18 and a carrier therefor.

30. A method for detecting bilirubin in urine, which method comprises contacting a urine test sample with the test composition of claim 1 and observing any colorimetric response which results.

31. A method for detecting bilirubin in urine, which method comprises contacting urine test sample with the test composition of claim 11 and observing any colorimetric response which results.

32. A method for detecting bilirubin in urine, which method comprises contacting a urine test sample with the test composition of claim 13 and observing any colorimetric response which results.

33. A method for detecting bilirubin in urine, which method comrises contacting a urine test sample with the test device of claim 22 and observing any colorimetric response which results.

* * * * *